Dec. 26, 1961 H. H. CHASE Plant Pat. 2,112
FLOWERING DOGWOOD TREE
Filed April 15, 1960 2 Sheets-Sheet 1
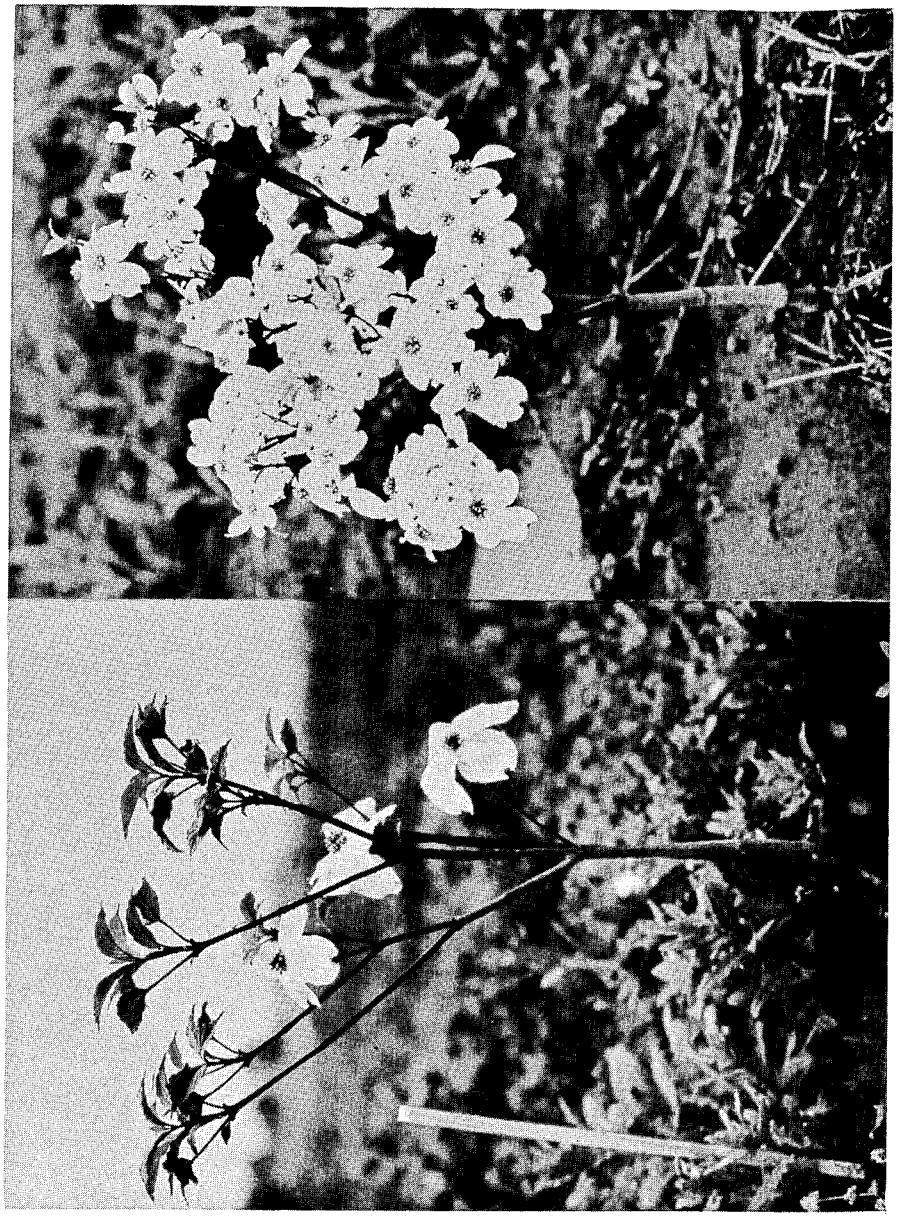
INVENTOR
Henry H. Chase
BY Robb & Robb
ATTORNEYS Dec. 26, 1961 H. H. CHASE Plant Pat. 2,112
FLOWERING DOGWOOD TREE
Filed April 15, 1960 2 Sheets-Sheet 2
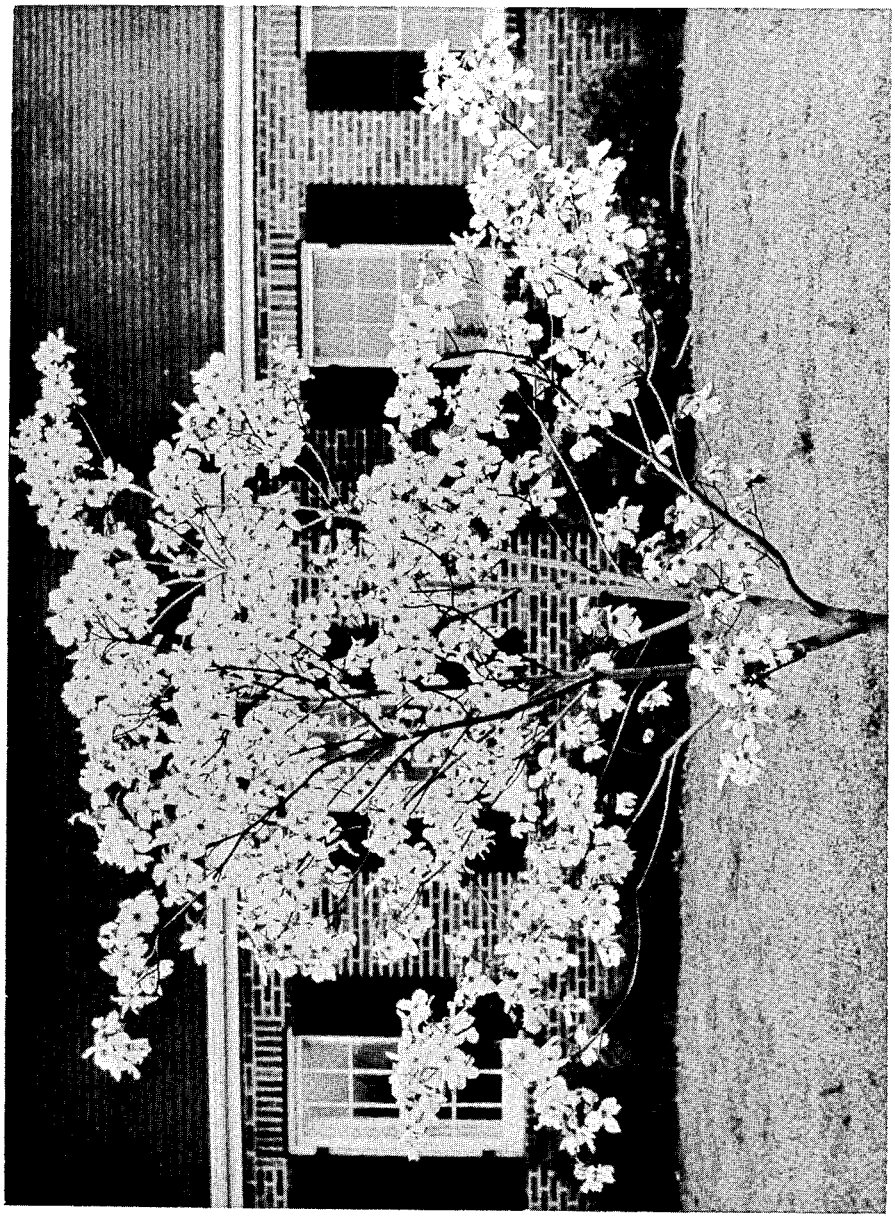
INVENTOR
Henry H. Chase
BY Robb & Robb
ATTORNEYS United States Patent Office Plant Pat. 2,112
Patented Dec. 26, 1961

2,112
FLOWERING DOGWOOD TREE

Henry H. Chase, Chase, Ala., assignor to Chase Nursery Company, Inc., Chase, Ala., a corporation of Alabama Filed Apr. 15, 1960, Ser. No. 22,654
1 Claim. (Cl. 47—60)

The present invention relates to a new and distinct variety of flowering dogwood tree which was discovered by me on the cultivated property of my assignee at Chase, Alabama, as a newly found seedling.

At the time of my initial discovery of this seedling, my attention was attracted to a small plant, approximately 3 feet tall, growing amongst a block of dogwoods of the species known as *Cornus florida* which were being grown under my direction and control on the nursery property of my assignee, as noted above. However, this single plant exhibited a substantially different habit of growth from that of the adjacent plants, and I therefore took steps to protect and preserve the small plant, keep it under observation, and later asexually reproduce the same. During the observations, I found that the original plant bore flowers at a very early age, had a more spreading habit of growth than the species *Cornus florida,* and in addition to a relatively rapid habit of growth, it bore flowers in unusually great abundance, said flowers being white in color and clothing the plant unusually well, thus giving the same an attractive mass effect. Excepting for these principal differences, the new seedling was generally similar to the *Cornus florida* species but, because of the substantial differences as aforementioned, I recognized the new seedling as a definite improvement over the regular dogwood species.

Asexual reproduction of the new seedling as performed by me by budding, at Chase, Alabama, has fully confirmed the novel characteristics and distinctions referred to above, and has conclusively proved that these characteristics and distinctions come true to form and are transmissible through succeeding propagations The accompanying drawings show typical young trees of my new dogwood variety at the respective ages of 1, 2, and about 5 years, in their order of size, with each view showing the early flowering habit, as well as the spreading habit of growth and an exceptionally free flowering habit.

The following is a detailed description of my new variety, with color terminology in accordance with Nickerson Color Fan, published by Munsell Color Co., Inc., of Baltimore Maryland, except where general color terms of ordinary dictionary significance are obvious, all as based upon observations of specimens growing outdoors at Chase, Alabama:

Parentage: Not definitely known but believed to be a seedling of the species *Cornus florida.*

Tree: Small; spreading; dense; hardy.

*Trunk.*—Stocky.

*Branches.*—Slender. Color—green when young but gray when mature.

*Twigs.*—Color—Dark Red, Plate 2.5R 3/7.

*Lenticels.*—1358 per node.

*Leaves.*—Simple; entire; medium thickness; abundant. Length—up to 6 inches. Width—up to 4 inches. Shape — ovate. Color — light green, comparable to *Cornus florida.* Margin—smooth edge, but undulate. Petiole—short. Glands—none. Stipules—none.

Flower buds. Extremely hardy; comparable in size, shape and color to *Cornus florida.*

Flowers:

*Blooming habit.*—First bloom usually begins in the early part of the month of April, but largely depends upon the weather.

*Quantity.*—Abundant.

*Size.*—Medium.

*Petalage.*—Number of petals—4 (bracts). Shape of petals—from oval to round; emarginate. Size of petals: length—up to 2 inches; width—up to 2 inches.

*Color of flowers.*—White.

I claim:

A new and distinct variety of flowering dogwood tree, substantially as herein shown and described, characterized particularly as to novelty by the unique combination of characteristics generally similar to the species *Cornus florida,* but having a more spreading and rapid habit of growth, a habit of commencement of bloom at an unusually early age, and an exceptionally free flowering habit, with an abundance of white blooms which create an attractive mass effect.

No references cited.